(12) United States Patent
Sun et al.

(10) Patent No.: US 8,372,415 B2
(45) Date of Patent: *Feb. 12, 2013

(54) WET GRANULATION USING A WATER SEQUESTERING AGENT

(75) Inventors: Thomas Sun, Palo Alto, CA (US); Ray Lo, San Leandro, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/559,097

(22) Filed: Jul. 26, 2012

(65) Prior Publication Data

US 2012/0288543 A1 Nov. 15, 2012

Related U.S. Application Data

(62) Division of application No. 12/266,337, filed on Nov. 6, 2008, now Pat. No. 8,263,122.

(60) Provisional application No. 60/986,237, filed on Nov. 7, 2007.

(51) Int. Cl.
*A61K 9/14* (2006.01)
*A61K 9/00* (2006.01)

(52) U.S. Cl. ........................ 424/400; 424/489

(58) Field of Classification Search ........................ None
See application file for complete search history.

(56) References Cited

U.S. PATENT DOCUMENTS

| | | | |
|---|---|---|---|
| 4,904,477 A * | 2/1990 | Ho et al. .................. | 424/465 |
| 5,358,652 A * | 10/1994 | Macpherson ............... | 508/271 |
| 5,763,172 A * | 6/1998 | Magda et al. .............. | 435/6.12 |
| 5,985,856 A * | 11/1999 | Stella et al. .............. | 514/80 |
| 6,238,677 B1 * | 5/2001 | Fanta et al. .............. | 424/400 |
| 6,716,453 B1 | 4/2004 | Harden et al. | |
| 7,060,827 B2 * | 6/2006 | Singh et al. .............. | 544/323 |
| 7,332,484 B2 * | 2/2008 | Singh et al. .............. | 514/230.5 |
| 7,563,892 B1 * | 7/2009 | Singh et al. .............. | 544/105 |
| 2003/0215502 A1 | 11/2003 | Pruss et al. | |
| 2006/0018972 A1 | 1/2006 | Hollenbeck | |
| 2006/0134148 A1 | 6/2006 | Hollenbeck | |
| 2006/0211657 A1 * | 9/2006 | Singh et al. .............. | 514/81 |
| 2006/0234983 A1 * | 10/2006 | Singh et al. .............. | 514/81 |
| 2007/0197419 A1 * | 8/2007 | Bianchi et al. .............. | 510/446 |
| 2011/0052685 A1 * | 3/2011 | Hou et al. .............. | 424/468 |
| 2011/0237609 A1 * | 9/2011 | Pimplaskar .............. | 514/266.4 |

FOREIGN PATENT DOCUMENTS

WO 2006/078846 7/2006

OTHER PUBLICATIONS

Airaksinen S, Karjalainen M, Kivikero N, Westermarck S, Shevchenko A, Rantanen J, Yliruusi J. Excipient selection can significantly affect solid-state phase transformation in formulation during wet granulation. AAPS PharmSciTech. Oct. 6, 2005;6(2):E311-22.*

Rahman BM, lbne-Wahed MI, Khondkar P, Ahmed M, Islam R, Barman RK, Islam MA. Effect of starch 1500 as a binder and disintegrant in lamivudine tablets prepared by high shear wet granulation. Pak J Pharm Sci. Oct. 2008;21(4):455-9.*

Waterman KC, Adami RC, Alsante KM, Antipas AS, Arenson DR, Carrier R, Hong J, Landis MS, Lombardo F, Shah JC, Shalaev E, Smith SW, Wang H. Hydrolysis in pharmaceutical formulations. Pharm Dev Technol. May 2002;7(2):113-46.*

Zografi, G. and Kontny, M.J. The Interactions of Water with Cellulose- and Starch-Derived Pharmaceutical Excipients. Pharmaceutical research 1986 3(4):187-194.*

Heinze, F. New Opportunities—Speciality Pregelatinised Starch Excipienhts. in Business Briefing:PharmaTech 2003 Technology and Service:1-5.*

Matt Duan, Jia Hu, Lan Zheng, Thomas Sun Purpose. Solution Kinetics and Solid State Stability of R788. 2007 AAPS Annual Meeting & Exposition. Contributed Papers:78 Physical Pharmacy I (Systens, Characteristics, PErformance). Abstract.*

Bajpai Malini: "Fostamatinib, a Syk inhibitor prodrug for the treatment of inflammatory disease," IDrugs: The Investigational Drugs Journal, Mar. 2009, vol. 12, No. 3, Mar. 2009, pp. 174-185.

Airaksinen, et al, "Excipient selection can significantly affect solid-state phase transformation in forumulation during wet granulation," AAPS PharmSciTech, Oct. 6, 2005; 6(2):E311-22.

Rahman, et al, "Effect of starch 1500 as a binder and disintegrant in lamivudine tablets prepared by high shear wet granulation," Pak J Pharm Sci, Oct. 2008; 21(4):455-9.

Waterman, et al, "Hydrolysis in pharmaceutical formulations," Pharm Dev Technol, May 2002; 7(2):113-46.

Zografi, et al, "The Interactions of Water with Cellulose- and Starch-Derived Pharmaceutical Excipients," Pharmaceutical research, 1986, 3(4):187-194.

Heinze, et al, "New Opportunities—Speciality Pregelatinised Starch Excipients," In Business Briefing:PharmaTech, 2003, Technology and Service:1-5.

Duan, et al, "Purpose. Solution Kinetics and Solid State Stability of R788," 2007 AAPS Annual Meeting & Exposition, Contributed Papers:78 Physical Pharmacy I (Systens, Characteristics, Performance). Abstract.

Sanchez, et al, "Gelatinized/freeze-dried starch as excipient in sustained release tablets," International Journal of Pharmaceutics, vol. 115, Issue 2, Mar. 7, 1995, pp. 201-208.

Ohmori, et al, Sustained-release phenylpropanolamine hydrochloride bilayer caplets containing the hydroxyproplymethylcellulose 2208 matrix., I. Formulation and dissolution characteristics, Chemical pharmaceutical bulletin (2000) vol. 48, Issue:5, pp. 673-677.

* cited by examiner

*Primary Examiner* — Robert A Wax
*Assistant Examiner* — Olga V Tcherkasskaya
(74) *Attorney, Agent, or Firm* — Travis Young; McDonnell Boehnen Hulbert & Berghoff LLP

(57) ABSTRACT

Disclosed are tablets comprising hydrolytically stable formulations of (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl phosphate disodium salt (Compound 1) prepared by a wet granulation process.

7 Claims, No Drawings

WET GRANULATION USING A WATER SEQUESTERING AGENT

CROSS REFERENCE TO RELATED APPLICATIONS

This application is a divisional of U.S. application Ser. No. 12/266,337, filed Nov. 6, 2008, which claims benefit under 35 U.S.C. §119(e) to application Ser. No. 60/986,237, filed Nov. 7, 2007, the contents of which are incorporated herein by reference in their entirety.

I. INTRODUCTION

1. Field of the Invention

This invention relates to pharmaceutical/formulation chemistry. The invention is understood to apply generally to formulations of hydrolytically unstable compounds. As a preferred embodiment, provided herein are higher density, hydrolytically stable formulations of (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl phosphate disodium salt (Compound 1) prepared by a wet granulation process. Such formulations inhibit degradation of Compound 1 during prolonged storage under ambient conditions. The formulations are useful for treating a variety of diseases including, but not limited to, lymphoma, immune (idiopathic) thrombocytopenia purpura (ITP), and rheumatoid arthritis (RA).

2. State of the Art

Compound 1 is currently in clinical studies for the treatment of a variety of diseases such as lymphoma, ITP and RA. Dosing is currently done with orally delivered tablets. Two sets of tablets used contain relatively high concentrations of Compound 1, i.e., 50 mg and 100 mg of active.

Compound 1, as synthesized, forms cotton like fluffy agglomerates with a very low bulk density (~0.15-0.30 g/mL). This characteristic confers poor powder flow and makes direct compression to tablets of the active impractical. Poor powder flow also results in a wide weight variation within the final product owing to variable fill of tablet dies, etc. Accordingly, it is desirable to formulate Compound 1 with higher density excipients such as fillers, binders, disintegrants, etc. which increase the bulk density and render the flow property adequate for compression into tablets.

Granulation is a process well known in the pharmaceutical industry, involving the preparation of aggregates ("granules") of fine particles of materials. Such granules are often compacted to form tablets. Formulations of pharmaceutical powders are granulated for a variety of reasons falling into two main classes: processing and formulation. Processing reasons are exemplified by the need for densification and aggregation. A dense, granular material will flow more evenly and fill dies on high speed tablet machines better and with greater consistency than a simple mixture.

One method of making granules is so called "wet granulation." In its simplest form, wet granulation involves the addition of a granulating fluid, commonly water, functioning as a granulating liquid, to a stirred powder comprising the materials to be granulated. The granulating liquid can be used alone or as a solvent containing a binder (also referred to as a "dissolved adhesive") which is used to ensure particle adhesion once the granule is dry. If the drying and subsequent handling is done with care, the aggregates will retain their integrity, giving a material which is both denser and more free flowing than the original material. Wet granulation has also been carried out with organic solvents or water-organic solvent mixtures, but organic solvents can present fire or toxicity hazards.

Wet granulation adds a significant degree of difficulty especially where the active agent is sensitive to water or heat. This invention is contemplated for hydrolytically unstable compounds generally. Compound 1, including its hexahydrate, is water sensitive and undergoes decomposition according to the following reaction scheme:

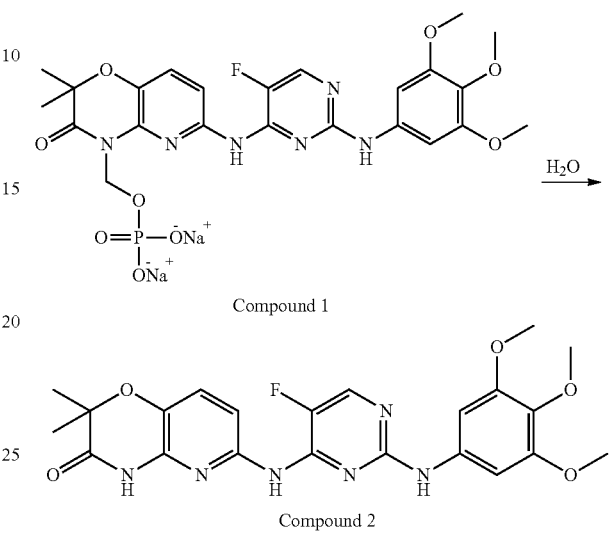

Compound 1

Compound 2

Compound 1 is a prodrug of Compound 2. It is preferable, then, that any wet granulation process employing water be done in a manner where little or no degradation of Compound 1 occurs either during the granulation, tablet formation, or storage so as to ensure that the proper systemic levels of Compound 2 are achieved.

In addition, it is preferable that the tablets formed be of sufficient hardness that they can be hand manipulated without breakage but disintegrate rapidly upon administration.

II. SUMMARY OF THE INVENTION

This invention is generally directed to hydrolytically stable formulations of hydrolytically unstable compounds, in particular to hydrolytically stable formulations of Compound 1 having a bulk density sufficient to form tablets having a hardness in the range of about 6 kp to about 30 kp, wherein said formulations are prepared in a wet granulation process. The formulation is then converted to tablets by conventional compression techniques. In some embodiments, the tablets have a hardness in the range of about 12 kp to about 20 kp, more preferably between about 14 kp to about 18 kp. In some preferred embodiments, the tablets have a hardness of about 16 kp. This invention is further directed to tablets formed from these hydrolytically stable formulations of Compound 1.

In particular, this invention is directed to the surprising and unexpected result that the inclusion of a higher bulk density, water sequestering agent with Compound 1 in the formulation, allows for use of water in a wet granulation process notwithstanding the hydrolytic instability of Compound 1.

This invention is further directed to the discovery that the bulk density of the resulting homogenous formulation correlates to compressed tablet hardness and that control of the bulk density to between about 0.35 g/mL and about 0.65 g/mL, and preferably between about 0.35 g/mL and about 0.60 g/mL, provides for tablets having a hardness in the range of about 6 kp to about 30 kp. Such tablets also exhibit at least 75% dissolution in less than 45 minutes in an aqueous solution maintained at pH 7.4 and a temperature of 37° C.±0.5° C.

This invention is still further directed to the discovery that the tablets of this invention have surprisingly long shelf-life with minimal degradation of Compound 1 during storage under ambient conditions. Accordingly, the tablets so formed are suitable for oral delivery.

In view of the above, in one of its formulation aspects, this invention is directed to a wet granulated formulation comprising water, an effective amount of Compound 1, a sufficient amount of a water sequestering agent to inhibit decomposition of Compound 1 wherein said formulation, after drying, has a bulk density sufficient to form tablets having a hardness in the range of about 6 kp to about 30 kp.

In one embodiment, the bulk density of the dried formulation is between about 0.35 g/mL to about 0.65 g/mL and preferably between about 0.35 g/mL to about 0.60 g/mL.

In another embodiment, the higher bulk density water sequestering agent is selected from the group consisting of starch (for example, partially pregelatinized starch), magnesium sulfate, calcium chloride, silica gel, kaolin and the like. Preferably, starch is employed and, more preferably, Starch 1500 available from Colorcon, Inc., West Point, Pa., USA, is employed. In some embodiments, the starch is derived from Maize (corn). In a preferred embodiment, the pregelatinized starch is derived from Maize.

In another embodiment, the formulation further comprises one or more fillers such as microcrystalline celluloses (e.g., Avicel PH 102 (FMC Newark, Del. 19711), Emcocel 90M (JRS Pharma Patterson, N.Y. 12563), etc.) and/or one or more lubricants (e.g., magnesium stearate) and/or one or more suspending/binding agents (e.g., Plasdone K29/32 (ISP Wayne, N.J. 07470)) and/or one or more disintegrants (e.g., Sodium Starch Glycolate (JRS Pharma Rosenberg, Germany), and the like.

In another aspect, this invention is directed to a tablet comprising water, an effective amount of Compound 1, and a sufficient amount of a water sequestering agent to inhibit decomposition of Compound 1, wherein said tablet has a hardness in the range of about 6 kp to about 30 kp.

In another embodiment, the tablets of this invention exhibit at least 75% dissolution in less than 45 minutes in an aqueous solution maintained at pH 7.4 and a temperature of 37° C.±0.5° C.

In another embodiment, the tablet further comprises one or more fillers such as microcrystalline celluloses (e.g., MCC Avicel PH 102, Emcocel 90M, etc.) and/or one or more lubricants (e.g., magnesium stearate) and/or one or more suspending/binding agents (e.g., Plasdone K29/32) and/or one or more disintegrants (e.g., ExploTab), and the like.

In one of its method aspects, this invention is directed to a method for formulating Compound 1 into a formulation suitable for tablet compression which method comprises:
  a) blending Compound 1 with starch and filler and optionally in the presence of one or more suspending/dispersing agents and/or more or disintegrants at an impeller speed sufficient, e.g. 155 to 405 rpm on a KG-5 High Shear Granulator, to form a homogenous mixture having a bulk density, after drying, sufficient to form tablets having a hardness of in the range of about 6 kp to about 30 kp;
  b) spraying between about 15% and 40% by weight of water into the homogenous powder mixture of a) above and mixing to form enlarged granules; and
  c) drying the enlarged granules produced in b) above until an LOD of between about 5% and about 11% is achieved, to provide dried granules.

The dried granules prepared in the methods above are typically between about 25 μm and about 900 μm in diameter.

In another of its method aspects, this invention further comprises milling the dried granules. In one embodiment, the dried granules are milled so that about 90 weight percent have a particle size between about 25 μm to about 900 μm in diameter.

In still another aspect, the dried, milled granules are mixed with a lubricant until homogenous, and then tabletting the resulting formulation. Suitable lubricants include stearic acid, colloidal silica and talc.

The tablets of this invention preferably comprise from about 25 mg to about 200 mg of Compound 1. More preferably, the tablets comprise between about 50 mg to about 100 mg of Compound 1 and, even more preferably, about 100 mg of Compound 1.

In another aspect, this invention provides a wet granulating process, comprising the following steps in the order shown:
  a) blending a composition comprising Compound 1 and a water sequestering agent to form a blended mixture;
  b) granulating the blended mixture of a) while adding water to form wet granules;
  c) drying the wet granules of b) at <65° C. until an LOD of between about 5% and 11% is achieved to provide dried granules; and
  d) blending a lubricant into the dried granules of c) to provide blended granules.

In another aspect, the method further comprises: (e) compressing the blended granules to form tablets.

In another aspect, this invention provides a wet granulated formulation comprising a therapeutically effective amount of Compound 1, a water sequestering agent, a lubricant, and about 5% to about 11% water. In another aspect, the formulation has a bulk density of between about 0.35 to about 0.60 g/mL. In another aspect, this invention provides a tablet formed by compressing the formulation.

III. DETAILED DESCRIPTION OF THE INVENTION

The invention provides higher density, hydrolytically stable formulations of Compound 1 prepared by a wet granulation process. Such formulations inhibit degradation of Compound 1 during prolonged storage under ambient conditions.

Definitions

The term "Compound 1" refers to the following compound and hydrates thereof including its hexahydrate:

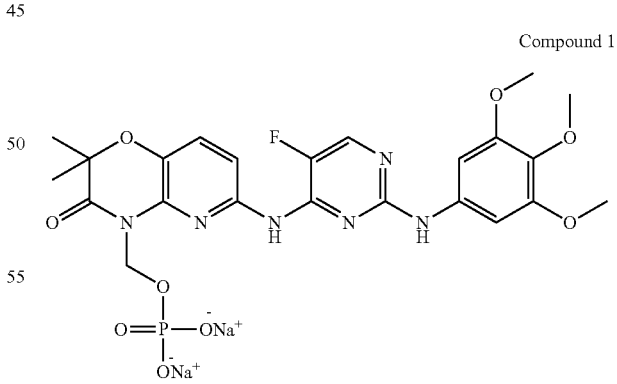

Compound 1

Compound 1 is sometimes referred to herein as (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl phosphate disodium salt. It is understood that the disodium salt is used for exemplary purposes only and that other pharmaceutically acceptable salts such as, but not limited to, the dipotassium salt or calcium salt, or magnesium salt can be used in place thereof. Compound 1 includes any of such other salts. Compound 1 also includes hydrates thereof, including but not limited to the hexahydrate of Compound 1.

Compound 1 is disclosed in U.S. patent application Ser. No. 11/453,731, published as US 2006-0234983 A1 which is incorporated by reference in its entirety.

The term "Compound 2" refers to the following compound and hydrates thereof:

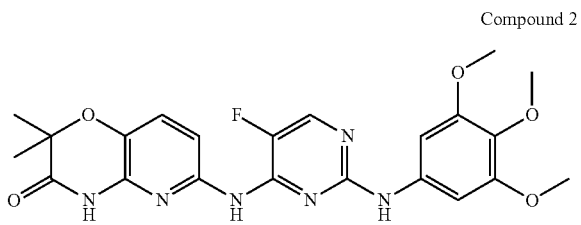 [SMILES: COc1cc(Nc2ncc(F)c(Nc3ccc4c(n3)NC(=O)C(C)(C)O4)n2)cc(OC)c1OC]

Compound 2

Compound 2 is sometimes referred to herein as 6-(5-fluoro-2-(3,4,5-trimethoxyphenylamino)pyrimidin-4-ylamino)-2,2-dimethyl-2H-pyrido[3,2-b][1,4]oxazin-3(4H)-one.

As used herein, the term "water sequestering agent" refers to pharmaceutically acceptable agents capable of absorbing water. Examples of suitable water sequestering agents include, but are not limited to, starch, calcium chloride, silica gel, kaolin, etc.

As used herein, the term "suspending/dispersing agent" refers to a pharmaceutically acceptable compound or composition that prevents or retards the settling of solid particles of the formulation of compound 1. Examples of suitable suspending/dispersing agents include, but are not limited to, Plasdone K29/32, Plasdone S-630, hydropropyl cellulose, methylcellulose, polyvinylpyrrolidone, aluminum stearate, hdroxypropylmethylcellulose and the like.

As used herein, the term "filler" refers to any pharmaceutically acceptable inert material or composition added to a formulation to add bulk. Suitable fillers include, for example, microcrystalline cellulose.

As used herein, the term "lubricant" refers to any pharmaceutically acceptable agent which reduces surface friction, lubricates the surface of the granule, decreases tendency to build-up of static electricity, and/or reduces friability of the granules. Lubricants can also play a related role in improving the coating process, by reducing the tackiness of binders in the coating. Thus, lubricants can serve as anti-agglomeration agents and wetting agents. Examples of suitable lubricants are magnesium stearate, stearic acid, or other hydrogenated vegetable oil or triglycerides.

As used herein, the term "disintegrant" refers to materials added to the composition to help it break apart (disintegrate) and release the medicaments. Examples of disintegrants include, but are not limited to, non-saccharide water soluble polymers, such as cross-linked povidine, can be added to the formulation to further enhance the rate of disintegration. Other disintegrants that can also be used include, e.g., croscarmellose sodium, sodium starch glycolate, and the like; see, e.g., Khattab (1992) J. Pharm. Pharmacol. 45:687-691.

As used herein, the term "bulk density" refers to the uncompressed, untapped powder bulk density, as measured by pouring an excess of powder sample through a funnel into a smooth metal vessel (e.g., a 500 mL volume cylinder), scraping off the excess from the heap above the rim of the vessel, measuring the remaining mass of powder and dividing the mass by the volume of the vessel.

As used herein, the term "tapped density" refers to density at constant volume. That is, a loose powdered sample (with a corresponding "bulk density") is placed in a vessel, e.g. in a graduated cylinder, and the vessel tapped on a surface, e.g. on the order of tens to hundreds of times, to compact the sample to constant volume. The density of the sample, once constant volume is reached via tapping, is the tapped density.

As used herein, the term "flow index" refers to a simple technique for the determination of powder flow characteristics.

The term "drying" and "dried" refer to a process which decreases the water content of a composition to a desired level.

The terms "compressing," "pressing," "molding" and "press molding" refer to the process of applying compressive force to a formulation (powder or granules), as within a die, to form a tablet. The terms "compressed tablet" and "pressed tablet" mean any tablet formed by such a process.

The term "tablet" is used in its common context, and refers to a solid composition made by compressing and/or molding a mixture of compositions in a form convenient for swallowing or application to any body cavity.

Formulations

Prior to tabletting, a wet granulated formulation is prepared, dried, milled and mixed, etc.

The wet granulated formulation comprises water, compound 1, and a sufficient amount of a higher bulk density water sequestering agent, such that after drying the wet formulation, the bulk density of the formulation is sufficient to provide for tablets having a hardness of between about 8 kp to about 24 kp.

The wet granulated formulation preferably comprises between about 10 to about 50 weight percent of Compound 1, about 100 to about 140 weight percent of a water sequestering agent based on the amount of Compound 1, and between about 90 to about 120 weight percent of water based on the total weight of the dry formulation prior to wet granulation.

Optional additives which can be added to the formulation include one or more of the following:
  a) fillers which, when employed, preferably range between about 30 to about 45 weight percent of the dry formulation prior to wet granulation;
  b) suspending/dispersing agents or binding agents which, when employed preferably range between about 2 to about 5 weight percent of the dry formulation prior to wet granulation;
  c) lubricants which, when employed, range from between about 0.25 and 2.0 weight percent of the dry formulation prior to wet granulation; and
  d) disintegrants which, when employed, range from between about 0.5 and 10.0 weight percent of the dry formulation prior to wet granulation;
  each of which is described above.

Preferably, the wet granulated formulation comprises Compound 1, a water sequestering agent, water, filler, suspending/dispersing agent and a disintegrant.

The wet formulation can additionally and optionally include a colorant, as long as it is approved and certified by the FDA. For example, exemplary colors include allura red, acid fuschin D, naphtalone red B, food orange 8, eosin Y, phyloxine B, erythrosine, natural red 4, carmine, to name a few.

Sweetening agents can also be added to the formulation or the outer core of the tablet to create or add to the sweetness. Saccharide fillers and binders, e.g., mannitol, lactose, and the like, can add to this effect. For example, cyclamates, saccharin, aspartame, acesulfame K (Mukherjee (1997) Food Chem.

Toxicol. 35:1177-1179), or the like (Rolls (1991) Am. J. Clin. Nutr. 53:872-878), can be used. Sweeteners other than sugars have the advantage of reducing the bulk volume of the tablet (core tablet and/or coat) and not effecting the physical properties of the tablet.

Manufacturing Processes

The preferred manufacturing process of this invention for wet granulation comprises preblending all of the required formulation components except water until homogenous. In one preferred embodiment, preblending is conducted in a granulator such as a Fielder PMA 300 High Shear Granulator with 36 inch impeller diameter, and preblending comprises mixing the components together at impellor speeds ranging between about 30 to about 70 rpm for a period of between about 0.5 to about 5 minutes.

Water is then sprayed onto/into the dry composition to form the wet granulated formulation described herein. The water is preferably added at a constant rate over a period of from about 1 kg/min to about 5 kg/min with either constant mixing during addition or mixing after addition. In either event, mixing is continued until the wet granulated composition is homogenous.

The wet granulated formulation is then dried using conventional techniques to reduce water content to a predetermined level. Preferably, the water content of the dried granulated formulation is between about 5% to about 11% by weight. Drying can be conducted at various temperatures and times. One skilled in the art could readily determine the appropriate drying times based on the initial water content, the desired final water content, and the drying temperature(s) employed.

The dried granulated formulation is milled using conventional techniques and machinery. In one embodiment, the formulation is milled through an appropriate mesh screen using commercially available milling equipment such as, e.g., Quadro Comil 196S (Quadro, Millbum, N.J.).

In one embodiment, the milled, dried granulated formulation is evaluated for degree of degradation of Compound 1 to Compound 2 as well as to confirm that the bulk density of the formulation will provide for tablet hardness of between about 8 to about 24 kp upon compression. Surprisingly, it has been found that the use of water in the wet granulation process as well as elevated temperatures during the drying protocol, does not significantly alter the amount of Compound 1 in the formulation. Typically, no more than 1% by weight of Compound 1 degrades during the granulation and drying process and even more preferably no more than 0.5% by weight.

The pressing or compression of the dried, granulated and milled formulation can be accomplished using any tablet press. Many alternative means to effect this step are available, and the invention is not limited by the use of any particular equipment. In a preferred embodiment, the compression step is carried out using a rotary type tablet press. The rotary type tabletting machine has a rotary board with multiple throughholes, or dies, for forming tablets. The formulation is inserted into the die and is subsequently press-molded.

The diameter and shape of the tablet depends on the die and punches selected for the compression of the milled and mixed formulation. Tablets can be discoid, oval, oblong, round, cylindrical, triangular, and the like. The tablets may be scored to facilitate breaking. The top or lower surface can be embossed or debossed with symbols or letters.

The compression force can be selected based on the type/model of press, a desired hardness of the resulting tablets of from about 8 kp to about 24 kp as well as other attributes, such as friability, disintegration or dissolution characteristics, etc. Preferred embodiment are described in the Examples below.

Measuring Tablet Properties

Tablet hardness is a physical strength measurement of a tablet. The resistance of a tablet to chipping, abrasion, or breakage under conditions of storage, transportation, and handling before usage depends on its hardness, or "crushing strength." The tablet "crushing" or "tensile" strength is defined as the force required to break a tablet by compression in the radial direction. It is typically measured using one of the many commonly available tablet hardness testers. For example, "Stokes" and "Monsanto" hardness testers measure the force required to break the tablet when the force generated by a coil spring is applied diametrically to the tablet. A "Strong-Cobb" hardness tester also measures the diametrically applied force required to break a tablet, the force applied by an air pump forcing a plunger against the tablet placed on an anvil. Electrically operated hardness testers, such as the Schleuniger apparatus (also known as a "Heberlein") can be used. See also, TS-50N, Okada Seiko Co., Japan; Bi (1996) Chem. Pharm. Bull. (Tokyo) 44:2121-2127.

Tablet friability is a physical strength measurement of a tablet, and is defined as the ability of the compressed tablet to resist abrasion and attrition. It is typically measured by turning tablets in a rotating vessel and determining weight loss (see De Jong (1987) Pharm Weekbl (Sci) 9:24-28). These rotating devices are called "friabilators." The friabilator provides frictional abrasion to the tablet sample and is used to measure the resistance to abrasion or attrition of tablets. The loss of weight is measured after a fixed number of revolutions of a drum rotating at a controlled rate.

Friabilator apparatus typically use a 285 mm drum of transparent synthetic polymer with polished internal surfaces. One side of the drum is removable. The tablets are tumbled at each turn of the drum by a curved projection that extends from the middle of the drum to the outer wall. The drum is attached to the horizontal axis of a device that rotates at about 25 to 30 rpm. Thus, at each turn, the tablets roll or slide and fall onto the drum wall or onto each other. Many such apparatus are commonly available, e.g., the Roche type friabilator (Van Kel Industries, Inc., Edison, N.J.); a Erweka Friability Apparatus (Erweka Instruments, Milford, Conn.) (Bi (1996) supra, Chowhan (1982) J. of Pharm. Sci. 71:1371-1375), and the like.

In one exemplary protocol, the standard United States Pharmacopia (USP) protocol for measuring friability is used. Briefly, the tablets are placed in a friabilator that is a 285 mm drum, about 39 mm in depth, of transparent synthetic polymer. The tablets are "tumbled" at each turn of the drum by a curved projection that extends from the middle of the drum. The drum is rotated for about four minutes at about 25 rpm, resulting in a total of 100 rotations. A minimum of about 20 tablets are used in any test, unless the tablets weigh over 650 mg, in which case only 10 tablets are used. After the allotted time, the tablets are removed from the friabilator, and, with the aid of air pressure or a brush, adhering particles and dust are removed, and remaining tablets are accurately weighed. Percent loss of weight is calculated.

Tablet dissolution is measured by the amount of time for 75% of the tablet to dissolve in an aqueous solution buffered to pH 7.4 and maintained at 37° C.±0.5° C. and paddle mixed at an rpm of 75.

Further examples of tablet formation are provided in U.S. Pat. No. 6,669,956 which is incorporated herein by reference in its entirety.

IV. EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

In the examples below as well as throughout the application, the following abbreviations have the following meanings. If not defined, the terms have their generally accepted meanings.

mL=Milliliter
g=Gram
mg=Milligram
rpm=revolutions per minute
min=Minute
mm=Millimeter
v/v=volume/volume
° C. degree Celsius
LOD=lost on drying
kp=kilopond (=1 kilogram (kg) or 9.807 Newtons of force)
API=active pharmaceutical ingredient Materials and Equipment Compound 1
Microcrystalline Cellulose Avicel 102 (Patheon)
Emcocel 90M, JRS Pharma E9B4B11X
Starch 1500, Colorcon, (Patheon)
Plasdone S-630, ISP
Plasdone K29/32, ISP (Patheon)
Explotab JRS Pharma (Patheon)
Magnesium Stearate, Mallinkrodt
Punch & Die for 500 mg tablet, 0.3510"×0.6299", Oval Shape
Balance, AX105, Mettler-Toledo Inc.
Balance, PG3001-S, Mettler-Toledo Inc.
Tablet Friabilator (USP), Pharma Alliance
Mini Blend V-Blender, Globe Pharma
USA Standard Testing Sieves
MiniGlatt Fluid Bed Dryer, Type 3, Glatt
Tablet Hardness Tester, Holland C40 Tablet Hardness Tester, Engineering Systems
Differential Scanning calorimeter, DSC Q100 by TA Instruments
Laboratory Humidity Chamber Mod. LH-1.5, Associated Environmental Systems
X-Ray Powder Diffraction, Miniflex Tabletop XRD System by Rigaku/MSC, The Woodlands, Tex.
Stokes B-2 Rotary Tablet Press
HPLC System, Waters with Photodiode Array Detector
Dissolution Tester, Sotax Dissolution with Rainbow Monitor System
Moisture Analyzer HB43, Mettler-Toledo Inc.
Flodex Powder Flow Tester, Hanson Research Corp.
High Shear Granulator, Mod. KG-5, Key International, Inc.

Example 1

Preparation of Final Blend

A 125 g batch of Compound 1 granules were prepared by mixing Compound 1 with all the excipients except magnesium stearate (listed in Table 1) on a paper tray using a spatula, granulated with approximately 130 g of water. Granules were dried in the fluid bed at 60° C. and collected at 7.3% and 6.5% LOD. They were then milled, and blended with 2% magnesium stearate for 2 minutes to make the final blend. The formulation is shown in Table 1. The final blend was characterized and pressed into tablets. The tablets were tested for potency and impurities, hardness and dissolution. Example 2 shows a final blend composition (Table 2) using a KG-5 High Shear Granulator.

TABLE 1

| Excipient | wt(g) |
| --- | --- |
| Compound 1 | 32.5 |
| Avicel PH102 | 38.75 |
| Starch 1500 | 40 |
| Plasdone K29/32 | 3.75 |
| Explotab | 7.5 |
| Magnesium Stearate | 2.5 |
| Total | 125 |

Example 2

Preparation of Final Blend Using a KG-5 High Shear Granulator

TABLE 2

| Excipient | wt(g) |
| --- | --- |
| Compound 1 | 130 |
| MCC Avicel PH102 | 157.5 |
| Starch 1500 | 160 |
| Plasdone K29/32 | 15 |
| Explotab | 30 |
| Magnesium Stearate | 7.5 |
| Total | 500 |

Example 3

Preparation of Compound 1 Powder Blend

Three 500 g batches of Compound 1 powder blends (see Table 3) were prepared according to the following method. A KG-5 High Shear Granulator with an 8-inch impeller diameter was used to preblend all ingredients (except magnesium stearate) at low (155 rpm), medium (405 rpm), or high (600 rpm) impeller speeds with the chopper speed of 1200 rpm for 2 minutes. Water was added at a rate of 30 to 31.5 g/min to the powder mix. After the full amount of water was added, the mixture was blended for an additional 2 minutes. The wet granules were dried with the MiniGlatt Fluid Bed Dryer at 60° C. to targeted LODs and the granule texture, size, shape, stickiness, etc visually inspected. Drying at various temperatures and times are evaluated also. The granules were milled through CoMill U3 with 0 32R mesh screen (0.0331 inch diameter holes), 1.5% magnesium stearate was added and mixed for 2 minutes in the V-blender to make the final blends. The final blends were checked for degradation by HPLC, and physical properties determined such as, Bulk Density, Tapped Density, Carr's Index, Hausner Ratio and Flow Index by Flodex. The final blends were compressed into 500 mg tablets using Stokes B-2 Rotary Press with 0.3071X0.6102 inches modified oval punches. The tablets were compressed with the same pressure settings to obtain maximum/achievable tablet hardness.

TABLE 3

| Excipient | wt(g) |
|---|---|
| Compound 1 | 130 |
| MCC Avicel PH102 | 157.5 |
| Starch 1500 | 160 |
| Plasdone K29/32 | 15 |
| Explotab | 30 |
| Magnesium Stearate | 7.5 |
| Total | 500 |

Carr's Index is a measure of compressibility of powder and defined as percent of (Tapped Density−Bulk Density)/Tapped Density. The higher the index, the more compressible of the powder and the poorer the flow. An index is 5 to 15% indicates excellent to good flowability. The Hausner Ratio is the ratio of Tapped Density to Bulk Density and is an assessment of interparticulate friction. A ratio of <1.6 is an indication of acceptable friction, in other words good powder flow. The maximum achievable hardness is defined as the hardness achieved with the maximum compression force.

Example 4

Physical Properties of Final Blend

Compound 1 (as the hexahydrate) was granulated with the excipients (except magnesium stearate) in Table 4. The physical properties of the final blend made by granulating Compound 1 with all the excipients together and drying to 6.5% LOD were measured and are shown in Table 5.

TABLE 4

| Excipient | wt(g) |
|---|---|
| Compound 1 | 32.5 |
| MCC Avicel PH102 | 38.75 |
| Starch 1500 | 40 |
| Plasdone K29/32 | 3.75 |
| Explotab | 7.5 |
| Magnesium Stearate | 2.5 |
| Total | 125 |

TABLE 5

| Bulk Density | 0.374 g/mL |
|---|---|
| Tapped Density | 0.420 g/mL |
| Carr's Index | 11.0% |
| Hausner Ratio | 1.12 |
| Flow Index | 16 mm |

The Carr's Index of 15% and a flow index of 16 mm indicate an excellent powder flow of the final blend.

Example 5

Maximum Achievable Hardness of Tablets

Tablets from final blends prepared as described in Example 4 with 7.27% and 6.47% LOD and were compressed and the hardness determined. The results are provided in Table 6. The tablet hardness was the maximum that was achievable. As demonstrated, tablets with hardness of 27.9 to 33.8 kp were obtained. All the tablets from these final blends appeared off-white and highly homogeneous. The final blend with 6.47% was compressed to tablets with hardness of 20 kp and 30 kp. The tablets displayed >75% dissolution after 30 minutes, indicating a large tolerance with respect to the hardness of tablets.

TABLE 6

| LOD of Final Blend = 7.27% | | | LOD of Final Blend = 6.47% | | |
|---|---|---|---|---|---|
| Weight, mg | Hardness, kp | Thickness, mm | Weight, mg | Hardness, kp | Thickness, mm |
| 500 | 27.9 | 4.98 | 505 | 33.8 | 5.06 |
| 504 | 29.8 | 5.05 | 506 | 32.2 | 5.08 |
| 501 | 29.1 | 5.04 | 505 | 33.8 | 5.08 |

Example 6

Stability of Compound 1 in Tablets

Tablets from Example 5 were stored under intensified shelf-life conditions (one month at 40° C. and 75% Relative Humidity) and analyzed for purity and potency by HPLC. Analysis results for tablets after one month at the aforementioned showed a purity of 98.8-99.1%.

Example 7

Dependence of Tablet Hardness on Density of Blend

Select batches of granules which were produced by methods described in Example 3, were further subjected to the various granulation parameters shown in Table 7. The impeller speed was varied and it was observed that low impeller speeds lead to less dense granules. In addition, the amount of water sprayed during the process was evaluated and it was found that less water sprayed may also help to lower the density of granules.

TABLE 7

| Batch | A | B | C |
|---|---|---|---|
| Batch Size, g | 500 | 500 | 450 |
| Impeller Speed, rpm | 405 | 600 | 155 |
| Chopper Speed, rpm | 2000 | 2000 | 1200 |
| Water added g/min | 30 | 30 | 31.5 |
| Water consumed, g | 250 | 260 | 185 |
| LOD of wet granules | 37.1% | 38.9% | 33.7% |
| LOD of dry granules | 6.5% | 6.0% | 6.6% |
| Bulk Density, g/mL | 0.570 | 0.621 | 0.505 |
| Tapped Density, g/mL | 0.632 | 0.674 | 0.583 |
| Hausner Ratio | 1.11 | 1.09 | 1.15 |
| Carr's Index | 9.81 | 7.86 | 13.4 |
| Flow Index | 14 mm | 14 mm | 14 mm |

* Batch C is a combination of three independent batches. Experimental procedures for Batch A, B, C are the same except the Impeller speed, chopper speed, rate and amount of water added.

All the granules possess excellent flow properties as measured by Hauser ratio, Can's index and flow index. The LOD of dry granules, 6.0 to 6.6%, is close to 7.1% as in the starting blend. These blends appeared ideal for tablet compression.

Tablets were compressed from these blends after blending with magnesium stearate at the maximum compression force. Results are summarized in Table 8. The less dense the blend, the harder the tablets. The blend with density of 0.65 g/mL resulted in tablets with the maximum hardness of 5-8 kp.

TABLE 8

| Tablet wt, mg | Hardness, kp | Thickness, mm |
|---|---|---|
| Maximum Tablet Hardness for Batch A: Bulk Density 0.570 g/Ml | | |
| 517 | 20.8 | 5.09 |
| 521 | 20.2 | 5.18 |
| 516 | 19.2 | 5.21 |

TABLE 8-continued

| Tablet wt, mg | Hardness, kp | Thickness, mm |
|---|---|---|
| Maximum Tablet Hardness for Batch B: Bulk Density 0.621 g/mL | | |
| 501 | 17.3 | 4.91 |
| 502 | 16.3 | 4.93 |
| 502 | 15.0 | 4.94 |
| Maximum Tablet Hardness for Batch C: Bulk Density 0.505 g/mL | | |
| 507 | 35.9 | 5.01 |
| 502 | 35.4 | 4.99 |
| 500 | 33.7 | 4.98 |

Example 8

Moisture Content (LOD) vs. Hardness of Tablets with Density of the Blend<0.55 g/mL The granules from Batch A (Example 7) were dried at 50° C., 60° C. and 70° C. to LOD of 6.4 to 6.8%. The dried granules were assayed by HPLC. The purity/impurity profiles remained the same for the three drying conditions. Compared to API, there was 0.15% decrease in purity and the same amount of increase in Compound 2. The tablets compressed from Batch A were dried and analyzed via HPLC and gave similar results to the granules. The dissolution of the tablets was >75% after 30 min.

Example 9

Moisture Content (LOD) vs. Hardness

Batch C (Example 7) was further dried in 6×65 g lots (Labeled C-1 to C-6) to LOD of 4.7, 5.6, 6.7, 7.6, 8.7 and 9.3%. All the dried granules were milled through CoMil with #25 mesh screen, and mixed with 1.5% magnesium stearate for 2 minutes. The physical properties of the final blends are summarized in Table 9.

TABLE 9

| | C-1 | C-2 | C-3 | C-4 | C-5 | C-6 |
|---|---|---|---|---|---|---|
| LOD, % | 4.70 | 5.58 | 7.55 | 6.74 | 8.74 | 9.33 |
| Sample Weight, g | 51.2 | 50.1 | 48.9 | 51.1 | 48.3 | 49.8 |
| Bulk Density, g/mL | 0.517 | 0.506 | 0.499 | 0.511 | 0.503 | 0.507 |
| Tapped Density, g/mL | 0.595 | 0.589 | 0.579 | 0.581 | 0.574 | 0.586 |
| Carr's Index | 13.1 | 14.1 | 13.8 | 12.1 | 12.4 | 13.5 |
| Hausner Ratio | 1.15 | 1.16 | 1.16 | 1.14 | 1.14 | 1.16 |

The final blends C-1-C-6 from Table 9 were compressed separately into 500 mg tablets under the same maximum compression force. LOD of the final blends, weight, hardness and thickness of the tablets are provided in Table 10.

TABLE 10

| | wt, mg | Hardness, kp | Thickness, mm |
|---|---|---|---|
| Tablet C-1 | 477 | 29.2 | 4.85 |
| LOD = 4.70% | 513 | 32.5 | 5.08 |
| | 514 | 34.4 | 5.09 |
| Tablet C-2 | 516 | 35.2 | 5.04 |
| LOD = 5.58% | 511 | 31.3 | 5.08 |
| | 500 | 31.9 | 4.99 |
| Tablet C-4 | 507 | 35.9 | 5.01 |
| LOD = 6.74% | 502 | 35.4 | 4.99 |
| | 500 | 33.7 | 4.98 |

TABLE 10-continued

| | wt, mg | Hardness, kp | Thickness, mm |
|---|---|---|---|
| Tablet C-3 | 502 | 33.0 | 4.94 |
| LOD = 7.55% | 500 | 33.0 | 4.92 |
| | 503 | 32.7 | 4.95 |
| Tablet C-5 | 502 | 29.5 | 4.93 |
| LOD = 8.74% | 500 | 29.0 | 4.94 |
| | 503 | 26.0 | 4.94 |
| Tablet C-6 | 506 | 26.9 | 4.97 |
| LOD = 9.33% | 505 | 26.4 | 4.97 |
| | 505 | 27.0 | 4.99 |

All of the U.S. patents, U.S. patent application publications, U.S. patent applications, foreign patents, foreign patent applications and non-patent publications referred to in this specification and/or listed in the Application Data Sheet are incorporated herein by reference, in their entireties.

Although the foregoing invention has been described in some detail to facilitate understanding, it will be apparent that certain changes and modifications may be practiced within the scope of the appended claims. Accordingly, the described embodiments are to be considered as illustrative and not restrictive, and the invention is not to be limited to the details given herein, but may be modified within the scope and equivalents of the appended claims.

What is claimed is:

1. A method for formulating (6-(5-fluoro-2-(3,4,5-trimethoxyphenylamino)pyrimidin-4-ylamino)-2,2-dimethyl-3-oxo-2H-pyrido[3,2-b ][1,4]oxazin-4(3H)-yl)methyl phosphate disodium salt into a formulation for tablet compression, which method comprises:
  a) blending (6-(5-fluoro-2-(3,4,5-trimethoxyphenylamino)pyrimidin-4-ylamino)-2,2-dimethyl-3-oxo-2H-pyrido[3,2-b][1,4]oxazin-4(3H)-yl)methyl phosphate disodium salt with starch and optionally at least one of a filler, a lubricant, a suspending/dispersing agent, a binding agent and a disintegrant, at an impellor speed sufficient to form a homogenous powder mixture having a bulk density after drying of about 6 kp to about 30 kp;
  b) spraying into the homogenous powder mixture between about 15% and about 40% by weight of water with respect to the total weight of the powder mixture plus water and mixing to form wet granules; and
  c) drying the wet granules until a loss on drying of between about 5% and about 11% is achieved, to provide dried granules.

2. The method of claim 1, wherein the dried granules are sized between about 25 μm to about 900 μm in diameter.

3. The method of claim 1 which further comprises milling the dried granules, to provide milled granules.

4. The method of claim 3, wherein the dried granules are milled so that about 90 weight percent of the milled granules have a particle size between about 25 to about 900 μm in diameter.

5. The method of claim 4, further comprising mixing the milled granules with a lubricant until homogenous, and then tabletting the resulting formulation.

6. A wet granulating process, comprising:
  a) blending a composition comprising (6-(5-fluoro-2-(3,4,5-trimethoxyphenylamino)pyrimidin-4-ylamino)-2,2-dimethyl-3-oxo-2H-pyrido[3,2-b ][1,4]oxazin-4(3H)-yl)methyl phosphate disodium salt and a sufficient amount of a water sequestering agent for inhibiting the decomposition of (6-(5-fluoro-2-(3,4,5-trimethoxyphenylamino)pyrimidin-4-ylamino)-2,2-dimethyl-3-oxo- 2H-pyrido [3,2-b][1,4]oxazin-4(3H)-yl)methyl phosphate disodium salt to form a blended mixture;
b) granulating the blended mixture while adding water to form wet granules;
c) drying the wet granules at 65° C. until a loss on drying of between about 5% and 11% is achieved to provide dried granules; and
d) blending a lubricant into the dried granules to provide blended granules.

7. The method of claim 6, further comprising:
compressing the blended granules to form tablets.

* * * * *